United States Patent
Yamasaki et al.

(10) Patent No.: US 7,018,647 B1
(45) Date of Patent: Mar. 28, 2006

(54) PATCHES FOR EXTERNAL USE

(75) Inventors: Keiko Yamasaki, Kagawa (JP); Mitsuji Akazawa, Kagawa (JP); Jutaro Shudo, Kagawa (JP); Keiji Nozaki, Tokyo (JP)

(73) Assignee: Teikoku Seiyaku Co., LTD, Kagawa (JP)

( * ) Notice: Subject to any disclaimer, the term of this patent is extended or adjusted under 35 U.S.C. 154(b) by 0 days.

(21) Appl. No.: 09/914,265

(22) PCT Filed: Oct. 25, 2000

(86) PCT No.: PCT/JP00/07451

§ 371 (c)(1),
(2), (4) Date: Sep. 5, 2001

(87) PCT Pub. No.: WO01/47559

PCT Pub. Date: Jul. 5, 2001

(30) Foreign Application Priority Data

Dec. 27, 1999 (JP) ................................. 11/368718

(51) Int. Cl.
*A61F 13/00* (2006.01)

(52) U.S. Cl. ...................... 424/449; 424/443; 424/448

(58) Field of Classification Search ................ 424/448, 424/449, 443
See application file for complete search history.

(56) References Cited

U.S. PATENT DOCUMENTS

| | | | | |
|---|---|---|---|---|
| 5,173,302 A | * | 12/1992 | Holmblad et al. | |
| 5,686,112 A | * | 11/1997 | Liedtke | ...................... 424/489 |
| 5,725,874 A | * | 3/1998 | Oda et al. | |
| 6,455,066 B1 | * | 9/2002 | Fischer et al. | |
| 6,562,363 B1 | * | 5/2003 | Mantelle et al. | ............ 424/434 |

FOREIGN PATENT DOCUMENTS

| | | |
|---|---|---|
| JP | 06-145053 | 5/1994 |
| JP | 11-171768 | 6/1999 |

* cited by examiner

*Primary Examiner*—Thurman K. Page
*Assistant Examiner*—Isis Ghali
(74) *Attorney, Agent, or Firm*—Wenderoth, Lind & Ponack, L.L.P.

(57) ABSTRACT

In order to provide an external skin patch having improved painkilling effect for pains accompanied by inflammation, such as chronic arthrorheumatism, arthrosis deformans or low back pain, an external skin patch is obtained by coating a drug-containing base on a substrate; the drug-containing base comprises an adhesive gel base containing a water soluble polymeric material, a crosslinking agent, water and a humectant as essential components, and a local anesthetic and a nonsteroidal antiphlogistic analgesic agent as medicinal components.

5 Claims, No Drawings

PATCHES FOR EXTERNAL USE

This application is a 371 of PCT/JP00/07451 filed Oct. 25, 2000.

TECHNICAL FIELD

The present invention relates to antiphlogistic analgesic external preparations. In particular, it relates to an external skin patch having greatly improved antiphlogistic analgesic effects which has a drug reservoir layer comprising a drug-containing base containing an adhesive gel base which contains a water soluble polymeric material, a crosslinking agent, water and a humectant as its essential components, and a local anesthetic and a nonsteroidal antiphlogistic analgesic agent as medicinal components.

BACKGROUND ART

At present, many kinds of nonsteroidal antiphlogistic analgesic agents having excellent anti-inflammatory, analgesic, and antipyretic actions, have been developed, and widely used against rheumatic disease, a postoperative pain or the pain after removal of a suture. Such a nonsteroidal antiphlogistic analgesic agent has been originally developed as an oral preparation, and has been employed as a useful therapeutic agent, however, the oral administration of such a nonsteroidal antiphlogistic analgesic agent may cause adverse effects such as gastrointestinal tract disorder etc.

On the other hand, an external preparation in the form of an ointment or a liquid drug has been developed for the treatment of arthrorheumatism, arthrosis deformans or low back pain, in order to change the administration route, so that the drug can be selectively delivered to the affected part, and the adverse effects caused from the oral administration, such as gastrointestinal tract disorder etc, can be alleviated. However, it is difficult to keep the applied dose or the applied area of these ointments and liquid drugs constant, and these ointments and liquid drugs often present a problem with use, i.e. the applied part becomes sticky, or these ointments and liquid drugs adhere to the clothes etc.

In contrast to this, patches are a preparation having the similar efficacy as those of the ointments and the liquid drugs. The patches are applied to a skin, and allow the drug to be transdermally absorbed into the body. The patches have various merits which are not owned by the ointments, such as accuracy of the applied dose, simplicity of the administration, and the hermeticity of the preparation applied to the affected part. In addition to these, the patches allow the drug to be continuously absorbed, thereby they show a prolonged action, therefore people has great expectations for the usefulness of the patches.

Presently, external skin patches containing three kinds of nonsteroidal agent (i.e. indomethacin, ketoprofen and flurbiprofen) have been on the market and their usefulness have been appreciated, as disclosed in the Japanese Unexamined Patent Application Publications No.2-212423, No.4-82828, No.8-319243, and No.9-124466.

At present, however, it is still difficult to provide analgesic effects against chronic pain coming from chronic arthrorheumatism, arthrosis deformans, low back pain and the like, even with these preparations. The reasons are believed to be as follows; the pain in the chronic arthrorheumatism, the arthrosis deformans and the low back pain are the somatic deep pain and the deep tissue causing such deep pain is not directly exposed to the external irritations, therefore the pain arises from fasciatonus or spasm caused by inflammation, patchion of nerve, nerve stimulus, bleeding, and edema etc. Either a local anesthetic or a nonsteroidal antiphlogistic analgesic agent when given alone for these symptoms does not work on both the inflammatory site and the peripheral nervous system, thereby the effect is limited. This is because, the local anesthetic reversibly anesthetizing a peripheral sensory nerve axis cylinder to lower or disappear the sensation of pain etc, and the nonsteroidal antiphlogistic analgesic agent working on a synapse on the path of pain, not on the sensory nerve fiber, to render the patient unaware of pain, have different mechanism of action on the pain respectively.

Accordingly, in the state of the art, a satisfactory external skin patch which has high painkilling effect for pains accompanied by inflammation, such as chronic arthrorheumatism, arthrosis deformans or low back pain, has not yet been developed.

DISCLOSURE OF INVENTION

A purpose of the present invention is to provide an external skin patch having improved painkilling effect for pains accompanied by inflammation, such as chronic arthrorheumatism, arthrosis deformans or low back pain.

As a result of extensive study carried out to solve the above-mentioned problem, the present inventors have found that the external skin patch in which a material comprising an adhesive gel base containing a water soluble polymeric material, a crosslinking agent, water and a humectant as essential components blended with both a local anesthetic and a nonsteroidal antiphlogistic analgesic agent is coated on a substrate, has excellent drug release controlling function, and allows the drug to be transdermally absorbed for an extended length of time, and shows remarkable pain killing effect on the pain accompanied by inflammation such as chronic arthrorheumatism, arthrosis deformans or low back pain by the anti-inflammatory effect as well as the local analgesic effect, and came to achieve this invention.

Accordingly, the present invention provides an external skin patch, comprising a substrate and a drug reservoir layer coated on the substrate, in which the drug reservoir layer comprises a drug-containing base comprising an adhesive gel base containing a water soluble polymeric material, a crosslinking agent, water and a humectant as essential components, and a local anesthetic and a nonsteroidal antiphlogistic analgesic agent as medicinal components.

The present invention provides the above-mentioned external skin patch, in which the local anesthetic comprises one or more kinds of compounds selected from the group consisting of tetracaine, procaine, dibucaine, lidocaine, benzocaine, xylocaine, and pharmaceutically acceptable salts thereof.

The present invention provides the above-mentioned external skin patch, in which the nonsteroidal antiphlogistic analgesic agent comprises one or more kinds of compounds selected from the group consisting of indomethacin, ketoprofen, piroxicam, felbinac, bufexamac, suprofen, flurbiprofen, diclofenac, ibuprofen and pharmaceutically acceptable salts thereof.

The present invention provides any of the above-mentioned external skin patches in which the drug-containing base contains the local anesthetic in an amount of 0.1–50% by weight.

The present invention provides any of the above-mentioned external skin patches in which the drug-containing base contains the nonsteroidal antiphlogistic analgesic agent in an amount of 0.05–10% by weight.

The present invention will be explained in detail.

An external skin patch according to the present invention has a substrate and a drug reservoir layer coated on the substrate.

(1) Substrates

The substrate employed for the external skin patch according to the present invention, can be any substrate usually employed in the art for an external skin patch. Examples of such a substrate include polyester, polyvinyl chloride, lint, nylon, an unwoven fabric or a composite material thereof. If necessary, a liner of a suitable material (such as a polypropylene film, polyethylene film, polyurethane film and the like) can be attached to the surface of the drug reservoir layer in order to prevent evaporation of the water therefrom and to protect the layer. The thickness of the substrate is not particularly limited and can be appropriately chosen depending on the applications.

(2) Drug Reservoir Layer

The drug reservoir layer of the external skin patch of the present invention comprises a drug-containing base comprising an adhesive gel base and a local anesthetic and a nonsteroidal antiphlogistic analgesic agent as medicinal components.

<Adhesive Gel Base>

The adhesive gel base employed according to the present invention contains a water soluble polymeric substance, a crosslinking agent, water and a humectant as essential components.

Examples of the above-mentioned water soluble polymeric substance include gelatin, starch, agar, mannan, alginic acid, polyacrylic acid, a salt of polyacrylic acid, dextrin, methyl cellulose, hydroxypropyl cellulose, methyl cellulose sodium, carboxymethyl cellulose, carboxymethyl cellulose sodium, polyvinyl alcohol, polyvinyl pyrolidone, methyl vinyl ether-maleic anhydride copolymer, gum Arabic, gum tragacanth, karaya gum, locust bean gum, and the like.

These water soluble polymeric materials are mainly employed such that the other materials employed in the adhesive gel base can exhibit their physical properites and desired properties can be obtained. These materials can be used alone or in admixture of two or more kinds.

The amount of the above-mentioned water soluble polymeric materials added to the adhesive gel base is preferably 0.5–50% by weight, more preferably 5–25% by weight. The content of the water soluble polymeric material falling within the above-mentioned range is preferable since the water retaining properties, adhesion and feel on use are improved.

As the crosslinking agent according to the present invention, both organic and inorganic crosslinking agents can be employed, however, an aluminum compound is preferable. Examples of the aluminum compound include aluminum hydroxide, aluminum chloride, aluminum silicate hydrate, synthetic aluminum silicate, dry aluminum hydroxide gel, aluminum acetate, aluminum lactate, aluminum stearate, magnesium aluminometasilicate, dihydroxyaluminum aminoacetate etc. These crosslinking agents can impart an appropriate strength to the gel as an initial property, prevent the strength of the gel from lowering, as they carry out efficient crosslinking with the polymeric material, maintain the form retaining properties, improve the stability of the properties of the preparations with time, and improve the workability and feel on use. These crosslinking agents can be used alone or in admixture of two or more kinds.

The amount of the above-mentioned crosslinking agents in the adhesive gel base is preferably 0.001–10% by weight, more preferably it is 0.01–5% by weight.

As water according to the present invention, purified water, sterilized water or ion-exchanged water is preferably used. Water is employed for swelling the corneal layer of epidermis and for improving the permeation of the drug, and the amount of the water added to the adhesive gel base is preferably selected to be within a range of from 10 to 80% by weight, more preferably of from 20 to 60% by weight.

Examples of the humectant according to the present invention include polyhydric alcohols such as ethylene glycol, diethylene glycol, polyethylene glycol, glycerin, sorbitol, multitol, propylene glycol, and 1,3-butylene glycol, saccharides such as sodium hyaluronate, and a superabsorbent resin such as starch-acrylonitrile graft body, starch-acrylic acid graft body, starch-styrene sulfonic acid graft body, starch-vinyl sulfonic acid graft body, polyvinyl alcohol crosslinked body, polyethylene glycol diacrylate crosslinked body, acrylic acid-vinyl acetate saponified product and the like. These humectants are employed to maintain the water content in the adhesive gel base at a constant level, so that the adverse effect on the drug releasing rate to the skin, resulting from the evaporation of the water from the obtained external skin patch during its storage or use, can be reduced. These humectants can be used alone or in admixture of two or more kinds.

The amount of the above-mentioned humectants used in the adhesive gel base is preferably 0.01–80% by weight, more preferably it is 1–60% by weight.

<Local Anesthetic>

Preferable local anesthetics employed according to the present invention include, but not limited to, a compound selected from the group consisting of tetracaine, procaine, dibucaine, lidocaine, benzocaine, xylocaine, and pharmaceutically acceptable salts thereof. These can be used alone or in admixture of two or more kinds.

The amount of the local anesthetic contained in the drug-containing base is preferably 0.1–50% by weight, more preferably 2–20% by weight based on the total mount of the drug-containing base. The amount of the local anesthetic below this range is not preferable due to insufficient efficacy, but the amount above this range is not preferable either, since the same effect is obtained with the danger of a side effect.

<Nonsteroidal Antiphlogistic Analgesic Agent>

Preferable examples of the nonsteroidal antiphlogistic analgesic agents employed according to the present invention include indomethacin, ketoprofen, piroxicam, felbinac, bufexamac, suprofen, flurbiprofen, diclofenac, ibuprofen and pharmaceutically acceptable salts thereof, however, the nonsteroidal antiphlogistic analgesic agents employed according to the present invention are not limited to these. These can be used alone or in admixture of two or more kinds.

The content of the above-mentioned nonsteroidal antiphlogistic analgesic agent in the drug-containing base is preferably 0.05–10% by weight, more preferably it is 0.2–5% by weight based on the total amount of the drug-containing base. The amount of the nonsteroidal antiphlogistic analgesic agent below the above-mentioned range is not preferable due to insufficient efficacy, but an amount above the range is not preferable either, since the same effect is obtained with the danger of a side effect.

<Optional Component>

The adhesive gel base employed according to the present invention may include various additional components employed in an ordinary adhesive gel base, in addition to the essential components, i.e. the water soluble polymer, the crosslinking agent, water and the humectant. Examples of such optional component include, for example, solvents such as N-methyl-2-pyrolidone, crotamiton, N,N-dimethyl acetamide, benzyl alcohol, mint oil, and isopropyl myristate; aliphatic acids such as stearic acid and oleic acid; various surfactants including nonionic surfactants, anionic surfactants, cationic surfactants and amphoteric surfactants such as polyoxyethylene sorbitan fatty ester, polyoxy ethylene hardened castor oil, polyglycerin fatty ester; ethers such as polyoxyethylene isocetyl ether; and other antiseptics, stabilizers, perfumes, coloring matters, powders, absorbing assistants, and pH adjusters etc.

As medicinal components, in addition to the above-mentioned local anesthetics and the nonsteroidal antiphlogistic analgesic agents, other analgesic, antipruritic, astringent, antiphlogistic agents such as salicylic acid, and a derivative thereof, camphor, capsicum extract, 1-menthol and the like can be used in combination.

The amount of these variety of additives can be suitably decided depending on the types of each product. These agents can be subjected to an ordinary process and formulated into an external skin patch.

<Preparation of a Drug-Containing Base>

The drug-containing base according to the present invention comprises the above-mentioned adhesive gel base with which the local anesthetic and the nonsteroidal antiphlogistic analgesic agent are blended as medicinal components. The preparation of the above-mentioned drug-containing base is not particularly limited, and the constituents of the adhesive gel base, i.e. the water soluble polymeric material, the crosslinking agent, water, the humectant, the optional components employed if desired, and effective amounts of the local anesthetic and the nonsteroidal antiphlogistic analgesic agent are appropriately mixed, and homogeneously kneaded. The order of the blending is not particularly limited. The medicinal components can be previously dissolved in an appropriate solvent then mixed.

(3) External Skin Patch

The external skin patch according to the present invention can be produced by spreading and coating the drug-containing base prepared according to the above-mentioned process on an appropriate substrate to form a drug reservoir layer. The amount of the drug-containing base coated is usually within a rage of from 200 to 2000 $g/m^2$, preferably of from 500 to 1500 $g/m^2$.

BEST MODE FOR CARRYING OUT THE INVENTION

The present invention will be further illustrated with reference to the following Examples, however, this invention is not limited to these Examples. All the proportions shown in Examples and Comparative Examples are % by weight.

EXAMPLE 1

A drug-containing base having a formulation given in the Table 1 below was prepared. More specifically, lidocaine was dissolved in propylene glycol and sodium diclofenac was dissolved in N-methyl-2-pyrolidone. These solutions were kneaded with other reagents shown in Table 1 until the mixture showed homogeneity to give a drug-containing base. The drug-containing base thus obtained was spread on a nonwoven fabric at 1000 $g/m^2$, and a polypropylene liner was attached to it then it was cut to a size of 10×14 $cm^2$ to give an external skin patch.

TABLE 1

| Ingredient | Proportion |
|---|---|
| Sodium diclofenac | 1 |
| Lidocaine | 5 |
| Propylene glycol | 10 |
| N-methyl-2-pyrolidone | 5 |
| 70% sorbitol solution | 20 |
| Sodium polyacrylate | 5 |
| Carboxymethyl cellulose sodium | 4 |
| Dry aluminum hydroxide gel | 0.3 |
| Tartaric acid | 2.5 |
| Kaolin | 5 |
| Purified water | the remainder |
| Total | 100 |

EXAMPLE 2

A drug-containing base having a formulation given in the Table 2 below was prepared. More specifically, felbinac was dissolved in crotamiton and benzocaine was dissolved in propylene glycol. These solutions were kneaded with other reagents shown in Table 2 until the mixture showed homogeneity to give a drug-containing base. The drug-containing base thus obtained was spread on a nonwoven fabric at 1000 $g/m^2$, and a polypropylene liner was attached to it then it was cut to a size of 10×14 $cm^2$ to give an external skin patch.

TABLE 2

| Ingredient | Proportion |
|---|---|
| Felbinac | 0.5 |
| Benzocaine | 7 |
| Propylene glycol | 5 |
| Glycerin | 10 |
| 70% sorbitol solution | 15 |
| Sodium polyacrylate | 5 |
| Carboxymethyl cellulose sodium | 5 |
| Dihydroxy aluminum acetate | 0.2 |
| Diethanol amine | 0.5 |
| Crotamiton | 2 |
| Tartaric acid | 1.5 |
| Purified water | the remainder |
| Total | 100 |

EXAMPLE 3

A drug-containing base having a formulation given in the Table 3 below was prepared. More specifically, indomethacin was dissolved in crotamiton and dibucaine hydrochloride was dissolved in purified water in an amount of 10% by weight. These solutions were kneaded with other reagents shown in Table 3 until the mixture showed homogeneity to give a drug-containing base. The drug-containing base thus obtained was spread on a nonwoven fabric at 1000 $g/m^2$, and a polypropylene liner was attached to it then it was cut to a size of 10×14 $cm^2$ to give an external skin patch.

TABLE 3

| Ingredient | Proportion |
| --- | --- |
| Indomethacin | 0.6 |
| Dibucaine Hydrochloride | 6 |
| Propylene glycol | 5 |
| Crotamiton | 2 |
| Glycerin | 10 |
| 70% sorbitol solution | 15 |
| Sodium polyacrylate | 5 |
| Polyacrylic acid | 2 |
| Carboxymethyl cellulose sodium | 4 |
| Magnesium aluminometasilicate | 0.3 |
| Tartaric acid | 1.7 |
| Sodium edetate | 0.1 |
| Purified water | the remainder |
| Total | 100 |

EXAMPLE 4

A drug-containing base having a formulation given in the Table 4 below was prepared. More specifically, ketoprofen was dissolved in crotamiton and tetracaine hydrochloride was dissolved in purified water in an amount of 15% by weight. These solutions were kneaded with other reagents shown in Table 4 until the mixture showed homogeneity to give a drug-containing base. The drug-containing base thus obtained was spread on a nonwoven fabric at 1000 g/m$^2$, and a polypropylene liner was attached to it then it was cut to a size of 10×14 cm$^2$ to give an external skin patch.

TABLE 4

| Ingredient | Proportion |
| --- | --- |
| Ketoprofen | 0.5 |
| Tetracaine hydrochloride | 8 |
| Crotamiton | 2 |
| Glycerin | 5 |
| 70% sorbitol solution | 15 |
| Sodium polyacrylate | 2 |
| Polyacrylic acid | 5 |
| Carboxymethyl cellulose sodium | 5 |
| Dihydroxy aluminum acetate | 0.2 |
| Tartaric acid | 1.5 |
| Sodium edetate | 0.1 |
| Purified water | the remainder |
| Total | 100 |

EXAMPLE 5

A drug-containing base having a formulation given in the Table 5 below was prepared. More specifically, flurbiprofen was dissolved in N-methyl-2-pyrolidone, and procaine hydrochloride was dissolved in purified water in an amount of 20% by weight. These solutions were kneaded with other reagents shown in Table 5 until the mixture showed homogeneity to give a drug-containing base. The drug-containing base thus obtained was spread on a nonwoven fabric at 1000 g/m$^2$, and a polypropylene liner was attached to it then it was cut to a size of 10×14 cm$^2$ to give an external skin patch.

TABLE 5

| Ingredient | Proportion |
| --- | --- |
| Flurbiprofen | 0.4 |
| Procaine hydrochloride | 10 |

TABLE 5-continued

| Ingredient | Proportion |
| --- | --- |
| Propylene glycol | 5 |
| N-methyl-2-pyrolidone | 5 |
| Glycerin | 10 |
| 70% sorbitol solution | 15 |
| Sodium polyacrylate | 6 |
| Polyacrylic acid | 2 |
| Carboxymethyl cellulose sodium | 4 |
| Dry aluminum hydroxide gel | 0.3 |
| Tartaric acid | 1.5 |
| Sodium edetate | 0.1 |
| Purified water | the remainder |
| Total | 100 |

EXAMPLE 6

A drug-containing base having a formulation given in the Table 6 below was prepared. More specifically, bufexamac was dissolved in N-methyl-2-pyrolidone and xylocaine was dissolved in purified water in an amount of 10% by weight. These solutions were kneaded with other reagents shown in Table 6 until the mixture showed homogeneity to give a drug-containing base. The drug-containing base thus obtained was spread on a nonwoven fabric at 1000 g/m$^2$, and a polypropylene liner was attached to it then it was cut to a size of 10×14 cm$^2$ to give an external skin patch.

TABLE 6

| Ingredient | Proportion |
| --- | --- |
| Bufexamac | 0.6 |
| Xylocaine | 8 |
| Propylene glycol | 5 |
| N-methyl-2-pyrolidone | 5 |
| Glycerin | 12 |
| 70% sorbitol solution | 14 |
| Sodium polyacrylate | 5 |
| Polyacrylic acid | 3 |
| Carboxymethyl cellulose sodium | 5 |
| Dry aluminum hydroxide gel | 0.3 |
| Tartaric acid | 1.2 |
| Sodium edetate | 0.1 |
| Purified water | the remainder |
| Total | 100 |

COMPARATIVE EXAMPLE 1

An external skin patch was prepared in the same production process employed in Example 1 except that the same amount of purified water was blended instead of sodium diclofenac.

COMPARATIVE EXAMPLE 2

An external skin patch was prepared in the same production process employed in Example 1 except that the same amount of purified water was blended instead of lidocaine.

COMPARATIVE EXAMPLE 3

An external skin patch was prepared in the same production process employed in Example 3 except that the same amount of purified water was blended instead of indomethacin.

COMPARATIVE EXAMPLE 4

An external skin patch was prepared in the same production process employed in Example 3 except that the same amount of purified water was blended instead of dibucaine hydrochloride.

TEST EXAMPLE

The external skin patches obtained in Examples 1 and 3 and Comparative Examples 1–4 were administered randomly to volunteers each having low back pain (i.e. plastered on the affected part) and an organoleptic examination was carried out. The duration of the administration was 12 hours a day and the test was carried out for 7 days. After the test, volunteers rated the results on a 1-to-4 scale ("complete remission", "effective", "unchanged" and "aggravation".) After 1 week of drug withdrawal, the same test was repeated until all the external skin patches were evaluated. The results are given in Table 7.

TABLE 7

|  | Ex. 1 | Ex. 3 | C. Ex. 1 | C. Ex. 2 | C. Ex. 3 | C. Ex. 4 |
| --- | --- | --- | --- | --- | --- | --- |
| Complete Remission | 7 | 5 | 0 | 3 | 0 | 0 |
| Effective | 2 | 5 | 2 | 5 | 3 | 7 |
| Unchanged | 1 | 0 | 8 | 2 | 6 | 3 |
| Aggravation | 0 | 0 | 0 | 0 | 1 | 0 |

As shown above, the amelioration ratio (effective or higher) of the external skin patches of Examples 1 and 3, and Comparative Examples 1–4 after 1 week was respectively 90% (9/10), 100% (10/10), 20% (2/10), 80% (8/10), 30% (3/10), and 70% (7/10), and the ratio of the Complete Remission was respectively 70% (7/10), 50% (5/10), 0% (0/10), 30% (3/10), 0% (0/10), and 0% (0/10).

This shows that the external skin patch in which a local anesthetic as well as a nonsteroidal antiphlogistic analgesic agent are contained (Examples 1 and 3) are superior to the external skin patches including either a local anesthetic or a nonsteroidal antiphlogistic analgesic agent alone (Comparative Examples 1–4). In other words, the effectiveness of the external skin patch according to the present invention in which both the local anesthetic and the nonsteroidal antiphlogistic analgesic agent are contained in combination was confirmed.

INDUSTRIAL APPLICABILITY

An external skin patch according to the present invention comprising a drug reservoir layer coated on a substrate, the drug reservoir layer comprising an adhesive gel base containing a water soluble polymeric material, a crosslinking agent, water and a humectant as essential components, and a local anesthetic and a nonsteroidal antiphlogistic analgesic agent as medicinal components, shows remarkable pain killing effect on the pain accompanied by inflammation such as chronic arthrorheumatism, arthrosis deformans or low back pain.

What is claimed is:

1. An external skin patch, comprising a substrate and a drug reservoir layer coated on the substrate, in which the drug reservoir layer comprises (1) an adhesive gel base which comprises a water soluble polymeric material, a crosslinking agent, 20 to 60% by weight of water based upon the total weight of the adhesive gel base and a humectant as essential components, together with (2) medicinal components comprising a local anesthetic and a nonsteroidal antiphlogistic analgesic agent, wherein the crosslinking agent is selected from the group consisting of aluminum compounds, wherein the humectant is selected from the group consisting of polyhydric alcohols, saccharides and superabsorbent resins, wherein the local anesthetic is selected from the group consisting of tetracaine, procaine, dibucaine, benzocaine, xylocaine, and pharmaceutically acceptable salts thereof, and wherein the nonsteroidal antiphlogistic analgesic agent is selected from the group consisting ketoprofen, piroxicam, felbinac, bufexamac, suprofen, flurbiprofen, ibuprofen, and pharmaceutically acceptable salts thereof.

2. The external skin patch according to claim 1, wherein the local anesthetic is present in an amount of 0.1–50% by weight.

3. The external skin patch according to claim 1, wherein the nonsteroidal antiphlogistic analgesic agent is present in an amount of 0.05–10% by weight.

4. The external skin patch according to claim 1, wherein the local anesthetic is selected from the group consisting of benzocaine and a pharmaceutically acceptable salt thereof.

5. The external skin patch according to claim 1, wherein the nonsteroidal antiphlogistic analgesic agent is selected from the group consisting of ketoprofen, felbinac, flurbiprofen, and a pharmaceutically acceptable salt thereof.

* * * * *